US006461376B1

(12) United States Patent
Beshore

(10) Patent No.: US 6,461,376 B1
(45) Date of Patent: Oct. 8, 2002

(54) TANNING APPARATUS AND HANDLE FOR USE THEREWITH

(76) Inventor: Burrus D. Beshore, 2054 S. Mountain View Rd., Sedalia, CO (US) 80135

( * ) Notice: Subject to any disclaimer, the term of this patent is extended or adjusted under 35 U.S.C. 154(b) by 57 days.

(21) Appl. No.: 09/790,768

(22) Filed: Feb. 21, 2001

(51) Int. Cl.$^7$ ................................................. A61N 5/06
(52) U.S. Cl. ........................ 607/91; 607/94; 250/504 R
(58) Field of Search ............................. 607/80, 88, 89, 607/90, 91, 92, 93, 94, 95; 250/504 R, 493.1, 494.1, 455.11

(56) References Cited

U.S. PATENT DOCUMENTS

| 4,100,475 | A | * | 7/1978 | Blaisdell et al. ............. 250/455 |
| 4,993,091 | A | * | 2/1991 | Draper et al. ................... 5/487 |
| 5,484,081 | A | | 1/1996 | Jahn |
| 5,683,437 | A | * | 11/1997 | Doty ............................ 607/91 |
| 5,725,565 | A | * | 3/1998 | Smith ........................... 607/88 |
| 6,139,568 | A | | 10/2000 | Doty |
| 6,402,774 | B1 | * | 6/2002 | Caldironi ..................... 607/91 |

OTHER PUBLICATIONS

Smart Tan '98 International Convention & Trade Show Supplement to Tanning Trends publication, provided by International Smart Tan Network Inc., of 3101 Page Ave., Jackson, MI 49203–2254.

Tanning Trends publication, May 2000 issue, provided by International Smart Tan Network Inc., 3101 Page Ave., Jackson, MI 49203–2254.

* cited by examiner

*Primary Examiner*—Pamela Wilson
(74) *Attorney, Agent, or Firm*—Timothy J. Martin; Michael R. Henson; Mark H. Weygandt

(57) ABSTRACT

A tanning apparatus with first and second tanning units movable between an open position to provide access to an interior and a closed position to enclose the interior and define a tanning chamber. Ultraviolet lamps are supported on one of the tanning units, and a control switch operates to generate ultraviolet radiation within the tanning chamber for a selected time interval. At least one handle projects away from a mounting surface for one of the units, and includes at least one mount and a grasping member connected to the mount so that the individual's arms can be elevated to promote exposure to radiation on a first region of the individual's body between the arm and torso during a tanning session. A method of promoting exposure to ultraviolet radiation is also provided, as well as a handle for use by the individual during a tanning session and a tanning apparatus.

26 Claims, 4 Drawing Sheets

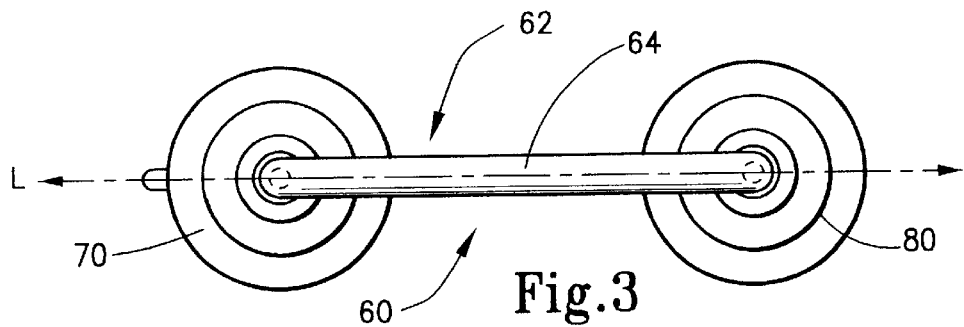
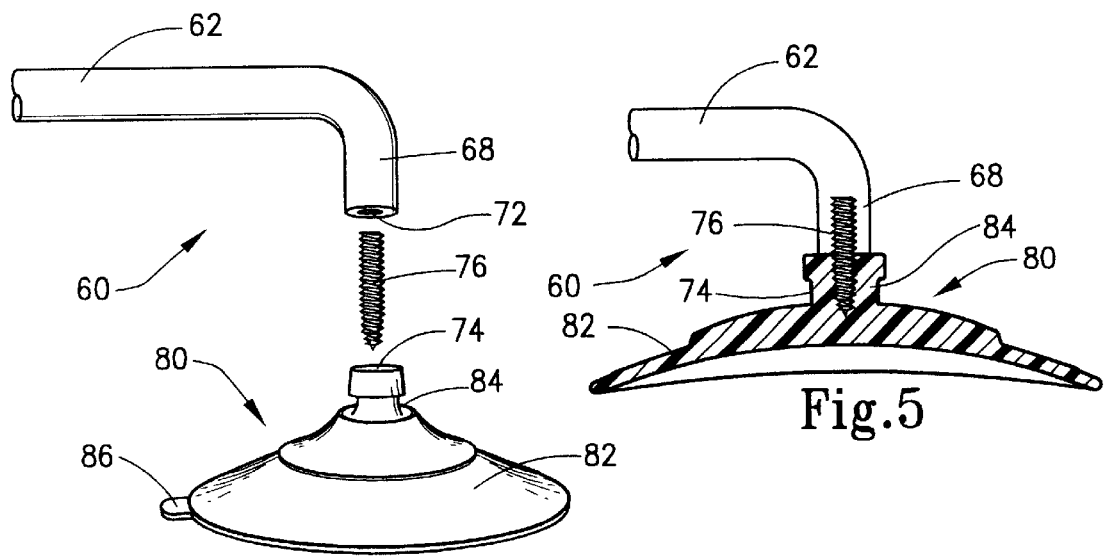
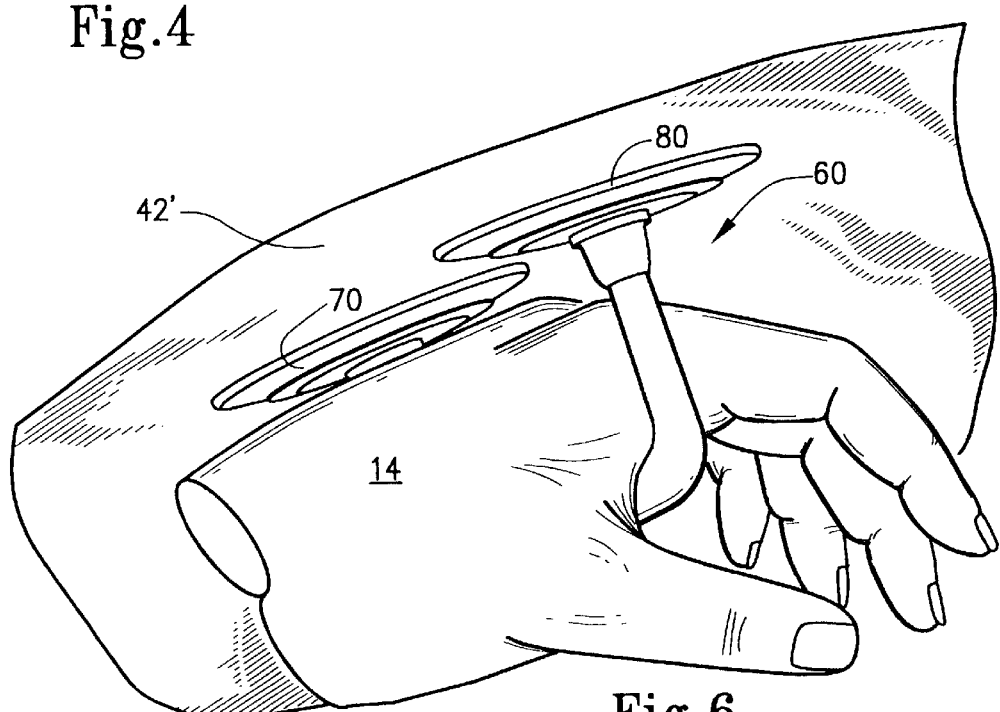

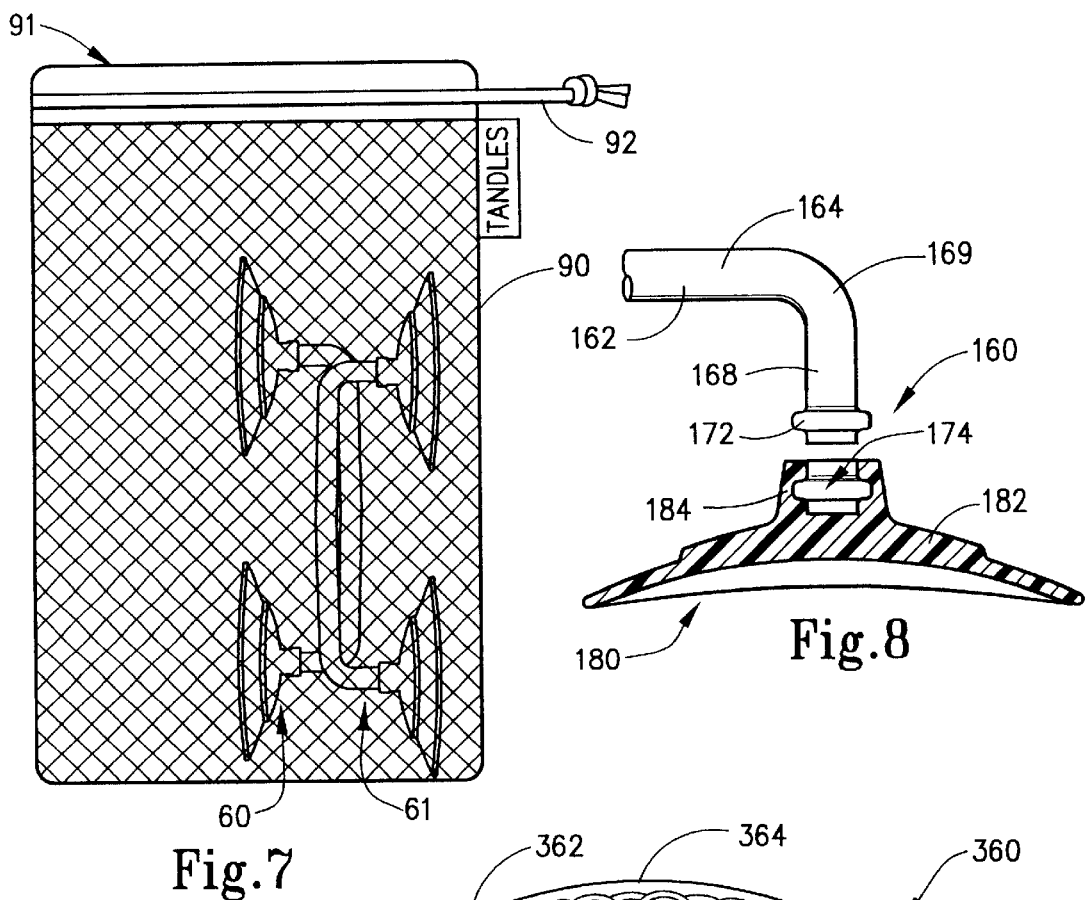
Fig.7
Fig.8
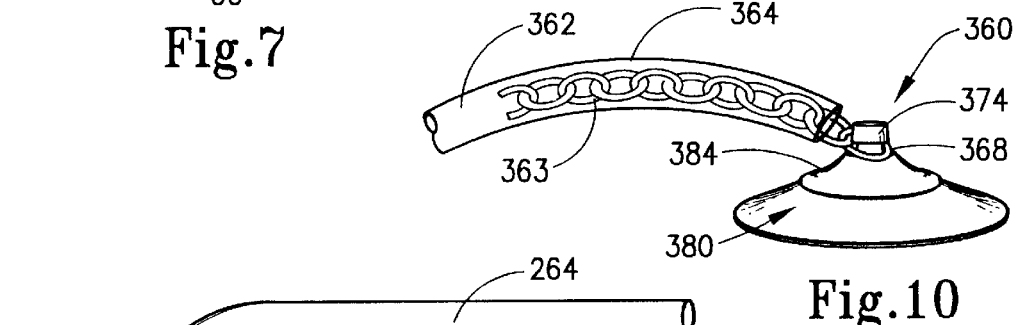
Fig.10
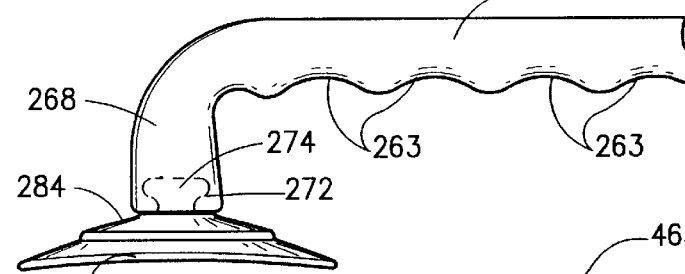
Fig.9
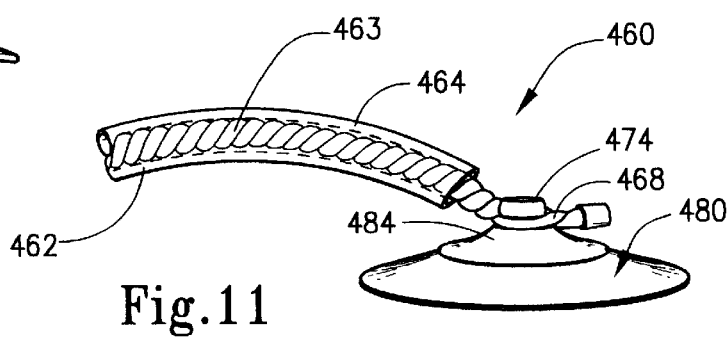
Fig.11

TANNING APPARATUS AND HANDLE FOR USE THEREWITH

FIELD OF THE INVENTION

The present invention broadly relates to accessory items for use in conjunction with a tanning apparatus. More particularly, the present invention concerns handles which may be incorporated into a tanning apparatus to support ones arms in an elevated position during a tanning session, as well as a methodology for doing the same.

BACKGROUND OF THE INVENTION

Each year thousands of individuals venture outdoors where they are exposed to sun light. Individuals are repeatedly exposed to the sun's rays by virtue of activities which may be recreational, leisure-oriented or work-related. For many, an important aspect of their recreational activities is obtaining a suntan, particularly for those who frequent beaches or swimming pools. Each year, for example, sun bathers line beaches on chairs or towels to spend hours in the sun in an effort to achieve the ideal tan.

Obtaining an ideal tan has long been a very popular recreational past time for many. In many societies, tanning is considered to be fashionable and is believed to make a person look healthier. This to a large extent contributes to the popularity of tanning. Despite its growing popularity, however, the public in recent years has been better informed about the potentially unhealthy effects of tanning. Medical advances have allowed scientists to more accurately pin point the causes of sun burns, and studies have indicated that sun burn can cause premature aging of the skin and increase the risk of skin cancers such as melanoma. More specifically, studies have shown that sun burns result from over-exposure to the sun's ultraviolet (UV) rays, and specifically the shorter wavelengths found in the UVB region of the ultraviolet spectrum which penetrates deeper into the layers of the skin, thereby playing a more significant role in skin cancer than other regions of the electromagnetic spectrum.

As a result of these studies, the consumer market has been infiltrated with various types of accessory items formulated to alleviate the undesirable effects attributed to over-exposure to ultraviolet radiation. These various types of treatments include sunscreens with different skin protection factor (SPF) ratings, lotions, eyewear, etc. This increased awareness has also prompted many to avoid long periods of exposure to the sun's rays, or avoid the sun altogether.

In recent years, one alternative to venturing outdoors to obtain a suntan is through the utilization of an indoor tanning apparatus, such as a tanning bed, an upstanding tanning unit, or even a tanning chair. These types of tanning apparatus employ artificial ultraviolet light and are very popular, especially in the winter months when a natural tan cannot be readily acquired and particularly in those areas where the summer tanning season is relatively short. Although the result is an artificial tan, the advances in this field are constantly improving such that it can be difficult to ascertain whether one's skin tone is a result of natural tanning or artificial tanning. Accordingly, tanning parlors and salons provide customers with a very appealing alternative from both a medical and convenience stand point. At a tanning salon, customers can also achieve a desired tan in generally less time than would otherwise be required outdoors. Moreover, depending on the climate and one's accessibility to the various locations traditionally attributed with sun tanning, such as beaches and swimming pools, the convenience to a tanning salon can be a more time efficient and cost effective alternative.

In an effort to optimism one's tan such that it is more evenly distributed and natural looking, tanning salons offer a variety of different types of tanning bed apparatus. Whether constructed as a tanning bed or a tanning stand, the tanning apparatus generally resembles a clam shell structure having a first arcuately contoured tanning unit and a second arcuately contoured tanning unit which are connected by hinges such that the apparatus can be opened and closed as desired. When in the open position a user can enter the apparatus to either lie down on the lower tanning unit or stand up inside the tanning booth. When the apparatus is closed, the units form an internal tanning chamber where the person to be tanned is surrounded by tanning lamps. Generally also, the tanning apparatus includes a control panel having a variety of adjustment mechanisms to permit a user to vary the intensity of the lamps, control the length of time he or she spends in the tanning bed apparatus, provide audio entertainment, etc.

As mentioned above, an important objective is to obtain an overall tan which is evenly distributed over one's body so that it is more natural looking. However, it is not uncommon for one utilizing a tanning apparatus to experience white stripping or blank spots in those areas of one's body which are not directly exposed to the artificial ultraviolet light. One of the most prone areas is in the region of the armpits since one's natural tendency is to relax the arms next to the side of one's body during use of the tanning apparatus. When this is done, white stripping also occurs where one's hand rests on the body. Presently, the most practical way of combating this is for one to continually reorient oneself during the tanning session so that one's extremities do not interfere with the exposure to the artificial ultraviolet rays. This might be accomplished, for example, by periodically elevating one's arms to a more appropriate position. However, continually reorienting oneself may exacerbate the inconsistency of the tan, not to mention the discomfort it causes to the individual.

Accordingly, there remains a need to provide new and improved accessory item for use in a tanning apparatus, such as a tanning bed unit, an upright tanning stand unit, or even a tanning chair, which allows one to comfortably and selectively position one's arm within the tanning apparatus to alleviate the occurrence of white stripping. There is a further need to provide a tanning apparatus which incorporates structure to accommodate this capability, as well as a methodology for comfortably retaining and repositioning one's arms in an elevated position while in a tanning apparatus to alleviate the occurrence of white stripping. The present invention is directed to meeting these needs.

SUMMARY OF THE INVENTION

It is an object of the present invention to provide a new and useful tanning apparatus for artificially tanning an individual.

Another object of the present invention is to provide a new and useful handle which is adapted for use by an individual during an artificial tanning session within a tanning apparatus to support the individual's arm(s) in an elevated position relative to the individual's torso.

A further object of the present invention is to provide such a handle which, when in use, promotes exposure to ultraviolet radiation on a region of the individual's body between the arm(s) and the torso during the tanning session.

Still a further object of the present invention is to provide such a handle which is easy to use and relatively inexpensive to manufacture.

Yet another object of the present invention is to provide a pair of such handles that are comfortable to use and releasably detachable from an interior surface of a tanning apparatus so that they can be selectively positioned at desired locations within an interior of the tanning apparatus.

It is yet another object of the present invention to provide a new and useful method of promoting exposure to ultraviolet radiation on an individual's body during an artificial tanning session in a tanning apparatus.

In accordance with these objectives, the present invention on one hand provides a tanning apparatus, such as a tanning bed, a tanning stand or a tanning chair for artificially tanning an individual situated therein during a tanning session. The tanning apparatus broadly comprises first and second tanning units each having an associated first end and extending therefrom to terminate at an associated second end. At least a first one of these elongated tanning units is adapted to be situated on a support surface. The first and second tanning units are hingedly connected together so that they are movable with respect to one another between an open position to provide access to an interior of the tanning apparatus and a closed position wherein the tanning units enclose the interior to define a tanning chamber. A plurality of ultraviolet lamps are supported by one or more of these tanning units. A control switch is also supported by an associated one of the first and second units. This control switch is operative upon activation to cause the lamps to generate ultraviolet radiation within the tanning chamber for a selected interval of time.

At least one handle is disposed on and projects away from a mounting surface of a selected one of the first and second tanning units. This first handle includes at least one mount releasably attached to the mounting surface and a grasping member connected to the mount. The grasping member is adapted to be held by the individual thereby to support one of the individual's arms in an elevated position relative to the individual's torso and promote exposure to ultraviolet radiation on a first region of the individual's body between the arm and the torso during the tanning session.

Preferably also, a second handle is disposed on and projects away from the mounting surface. This second handle also includes at least one associated mount releasably disposed on the mounting surface and an associated grasping member disposed on the mount. This grasping member is also adapted to be held by the individual thereby to support another one of the individual's arms in an elevated position relative to the individual's torso and promote exposure to ultraviolet radiation on an associated second region of the individual's body between the arm and torso.

The present invention is also directed to a handle which is adapted for use by an individual during an artificial tanning session within a tanning apparatus, such as that discussed above, to support the individual's arm in an elevated position relative to the individual's torso. Here, the handle broadly comprises an elongated crosspiece, a first mount and a second mount. The elongated crosspiece includes a grip portion that extends along a longitudinal axis and a pair of legs each extending from respective ends of the grip portion. The first mount is disposed on one of these legs, while the second mount is disposed on another leg. Each of the mounts is operative to releasably attach to a respective interior mounting surface of the tanning apparatus so that the handle can be selectively positioned on the mounting surface and grasped by the individual to support the individual's arm in an elevated position and, thus, promote exposure to ultraviolet radiation between the individual's arm and torso during the tanning session.

Each of the legs preferably extends from the grip portion in a direction transverse to the longitudinal axis. The crosspiece may be either flexible or stiff in construction. Where the crosspiece is flexible, it may include a flexible cord having opposed cord ends secured to the first and second mounts, respectively, as well as a flexible sleeve surrounding a majority of a length of the cord between the opposed cord end portions. Alternatively, the crosspiece may include a chain having opposed end links attached to the first and second mounts, respectively, and a flexible sleeve surrounding a majority of the chain between the opposed end links.

Each of the mounts may be formed as a plastic suction cup, and is preferably formed of a flexible polyvinyl material which is resistive to deterioration over repeated exposure periods to ultraviolet radiation. The plastic suction cup includes a fruistoconical lower body portion adapted to releasably suction to the interior mounting surface of the tanning apparatus and an upper neck portion adapted to engage an associated one of the legs. To this end, each of the legs may include an associated surrounding flange and each upper neck portion may have a cavity formed therein which is sized and adapted to receive an associated flange so that the mounts are releasably disposed on their associated legs. Alternatively, each of the legs may be formed to include a leg cavity and each neck portion formed to include a nub that is releasably inserted into an associated leg cavity to attach the mounts to the legs. Yet another alternative is to provide a fastening element, such as a screw, which is operative to attach each leg to its associated mount.

The lower body portion of each mount may also incorporate a pull tab which protrudes therefrom, with this pull tab operative upon manipulation by the individual to facilitate detachment of the mount from the interior mounting surface. Preferably also, the grip portion of the crosspiece is contoured to include a plurality of recesses for accommodating the individual's fingers.

The present invention also provides a method for promoting exposure to ultraviolet radiation on an individual's body during an artificial tanning session in a tanning apparatus. Here, and as discussed above, the tanning apparatus includes a pair of tanning units movable with respect to one another between an open position to provide access to an interior of the tanning apparatus and a closed position wherein the tanning units enclose the interior to define a tanning chamber. A plurality of ultraviolet lamps are supported by at least one of the tanning units, and a control panel is operative upon activation to cause these lamps to generate ultraviolet radiation within the tanning chamber for a selected interval of time corresponding to a tanning session.

The methodology of the present invention broadly comprises the steps of entering the tanning apparatus, moving the tanning units from the open position to the closed position, attaching each of a pair of handles in a respective mounted state to an interior mounting surface of the tanning chamber, activating the control panel thereby to initiate the ultraviolet radiation, grasping each of the handles in such a manner that the individual's arms are supported in an elevated position relative to the individual's torso thereby to assume a tanning position wherein respective regions of the individual that are between the arms and torso are exposed to ultraviolet radiation, and remaining in the tanning apparatus for selected period of time corresponding to a length of the tanning session. The methodology may also incorporate the steps of periodically detaching the handles from the interior mounting surface during the tanning session and repositioning the handles on the interior mounting surface thereby to adjust the individual's tanning position and promote exposure to ultraviolet radiation on other regions of the individual between the arms and torso.

These and other objects of the present invention will become more readily appreciated and understood from a consideration of the following detailed description of the exemplary embodiments of the present invention when taken together with the accompanying drawings, in which:

BRIEF DESCRIPTION OF THE DRAWINGS

FIG. 3 is a top planer view of the representative handle shown in FIG. 2;

FIG. 4 is an exploded perspective view showing the attachment of one of the handle's mounts to its associated leg;

FIG. 5 is a side view in elevation and in cross-section showing the attachment of the handle's mount to its associated leg;

FIG. 6 is a perspective view showing the handle of FIGS. 2–5 in use on the interior mounting surface of the tanning apparatus in FIG. 1 to comfortably support the individual's left hand such that the individual's left arm is supported in an elevated position relative to the individual's torso during the tanning session;

FIG. 7 is side view in elevation showing a pair of handles conveniently received in a portable carrying pouch;

FIG. 8 is an exploded cross-sectional view showing one alternative construction for a handle, and specifically, the attachment of the mount to its associated leg;

FIG. 9 is a perspective view showing another alternative construction for the handle of the present invention;

FIG. 10 is a perspective view showing still another alternative construction for a handle according to the present invention;

FIG. 11 is a perspective view showing yet another alternative construction for a handle according to the present invention.

DETAILED DESCRIPTION OF THE EXEMPLARY EMBODIMENTS

Figure 1:
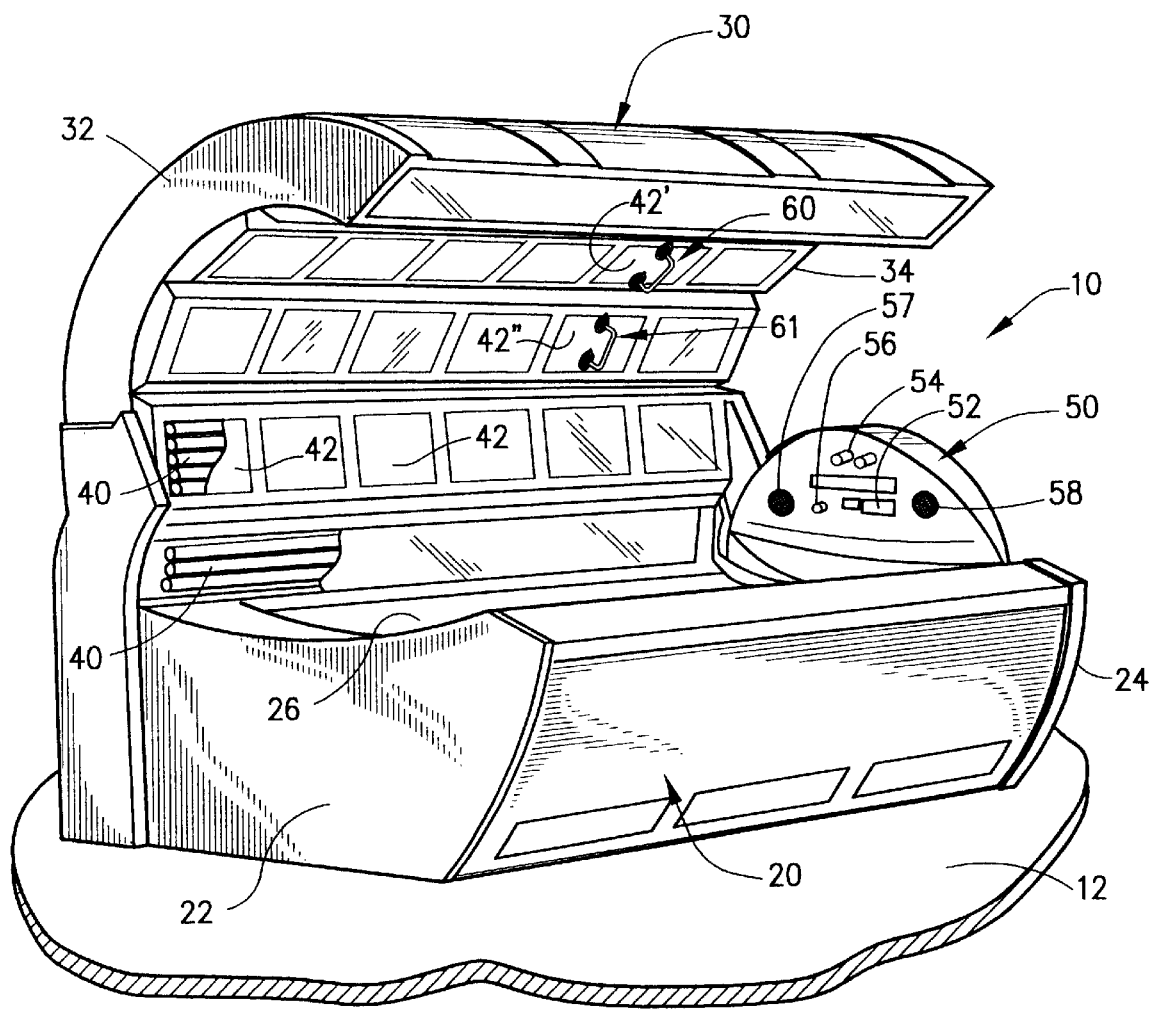
FIG. 1 is a perspective view of a representative tanning apparatus according to the present invention.

Referring now to the drawings, there is illustrated in FIG. 1 a perspective view of one exemplary embodiment of the present invention in the form of a tanning apparatus 10. Tanning apparatus 10 is particularly in the configuration of a tanning bed, although the ordinarily skilled artisan will readily appreciate that tanning apparatus 10 could take on the configuration of an upright tanning stand or even a tanning chair without departing from the inventive concepts herein. Accordingly, since a variety of different styles of these types of tanning apparatus configurations (i.e. bed, stand or chair) are available, the present invention should not be unduly limited to its application only in conjunction with the tanning bed apparatus 10 depicted in FIG. 1.

Tanning apparatus 10 is situated on a support surface 12 and broadly comprises a base unit 20, also referred to as a first unit, and an upper unit 30, also referred to as a second unit. Base unit 20 can have a suitable configuration such as the configuration generally shown in FIG. 1 so that it is elongated and extends between first and second ends 22 and 24, respectively. Upper tanning unit 30 also has a suitable configuration such as that shown in FIG. 1 so that it is elongated and extends between associated first and second ends 32 and 34, respectively. Since tanning apparatus 10 is in a configuration of a tanning bed, base unit 20 has an arcuately contoured bed 26 for comfortably supporting a user in a reposed position during a tanning session.

First and second tanning units 20 and 30 are hingedly connected to one another, as known in the art, so that they are movable with respect to one another between an open position as shown in FIG. 1 to provide access to an interior of the tanning apparatus 10 and a closed position (not shown) wherein the tanning units 20, 30 substantially enclose the interior and define a tanning chamber. A plurality of ultraviolet lamps, such as lamps 40, may be distributed throughout the tanning apparatus and supported by one or both of the first and second tanning units 20, 30. In FIG. 1, for example, ultraviolet lamps 40 are shown as bulbs which extend longitudinally along a side edge of tanning apparatus 10 as well as longitudinally between the first and second ends 32, 34 of arcuately contoured upper tanning unit 30. A plurality of cover panels 42 formed of ultraviolet transmissive material are also associated with the upper tanning unit 30 and extend over the ultraviolet lamps 40. It bears repeating that since tanning apparatus 10 can take on a variety of styles and configurations, the same also holds true for the array of ultraviolet lamps 40 associated therewith so that the manner of supporting the array of lamps 40 in FIG. 1 is for illustrative purposes only.

Tanning apparatus 10 also comprises a control panel 50, shown in FIG. 1 to be supported by the lower tanning unit 20. Control panel 50 includes a control switch 52 that is operative upon activation to cause the ultraviolet lamps 40 to generate ultraviolet radiation within the tanning chamber for a selected interval of time corresponding to a tanning session. Control panel 50 may also incorporate other features for varying the environment within the interior of the tanning apparatus 10. For illustrative purposes only, one such additional feature may include a radio having an adjustment knob 54, a volume control knob 56 and a pair of speakers 57 and 58.

While up to this point tanning apparatus 10 has been described as a conventional tanning bed as known in the art, it differs from these known devices in that it incorporates a pair of handles 60 and 61 which are releasably attachable to respective interior mounting surfaces of the tanning apparatus 10. More particularly, representative first handle 60 is releasably attachable to an associated interior mounting surface defined by smooth cover panel 42', while representative second handle 61 is releasably attachable to a respective interior mounting surface defined by cover panel 42". As shown in FIG. 7, a mesh bag 90 or the like may be provided for conveniently transporting handles 60 and 61 therein when the individual frequents a tanning salon. Mesh bag 90 is generally rectangular in configuration and is provided with a draw cord 92 for cinching the mouth 91 thereof closed for convenient transport.

Figure 2:
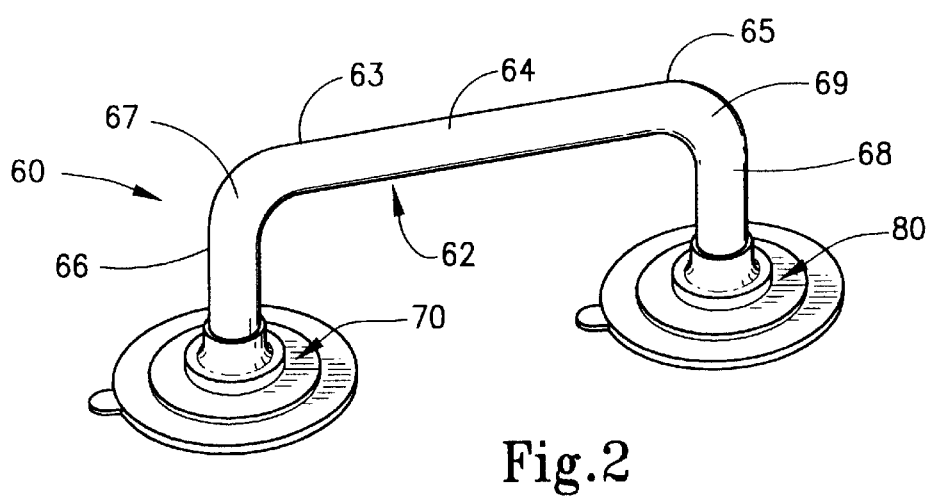
FIG. 2 is a perspective view of a representative one of the handles which are shown in FIG. 1 to be releasably mounted to an interior mounting surface of the tanning apparatus.

The construction for representative handle 60 in FIG. 1 may now be appreciated with reference to FIGS. 2–5. Of course, the ordinarily skilled artisan should readily appreciate that handle 61 in FIG. 1 would be constructed the same. Handle 60 may be part number 116.71 available from Hafele America Co. of Carson, Calif. Turning initially then to FIGS. 2 and 3, representative handle 60 comprises an elongated crosspiece 62 which includes a grip portion 64 extending along a longitudinally axis "L". Crosspiece 62 also includes a pair of legs 66 and 68 which extend from the grip portion 64. More particularly, a first leg 66 extends transversely from one end 63 of grip portion 64 and is joined thereto by a first shoulder 67, while a second leg 68 extends from another end 65 of grip portion 64 and is joined thereto by a second shoulder 69. A first mount 70 is disposed on first leg 66 and a second mount 80 is disposed on second leg 68. Each of mounts 70 and 80 is operative to releasably attach to the interior mounting surface 42' of tanning apparatus 10 in FIG. 1 so that handle 60 can be selectively positioned on mounting surface 42' and grasped by the individual.

FIGS. 4 and 5 illustrate one possible manner for attaching mount 80 to its associated leg 68. Though not shown, the attachment of first mount 70 to its associated first leg 66 would be the same. Mount 80 may be a plastic suction cup, and is preferably formed of a flexible polyvinyl material which is resistive to deterioration over prolonged and repeated exposure to ultraviolet radiation, such that it maintains its suctioning capability and does not crack. One such plastic suction cup which exhibits these performance capabilities is part number 32512-8, a medium suction cup with stud, available from the Adams Manufacturing Corp. of Portersville, Pa. As shown in the figures, the suction cup includes a frustoconical lower body portion 82 adapted to releasably suction to the interior mounting surface 42' of tanning apparatus 10 and an upper neck portion 84 which is adapted to engage leg 68. To accomplish this, the crosspiece 62 for handle 60 in FIGS. 2-5 is formed of a stiff plastic material having a cavity 72 formed in leg 68 which is adapted to threadedly receive a screw fastener 76. A similar hole 74 is also formed in the neck portion 84 of second mount 80 which is also adapted to threadedly receive fastener 76. Accordingly, once fastener 76 is threadedly inserted into leg cavity 72, mount 80 can be screwed onto fastener 76 to attach mount 80 to leg 68 in an attached state as shown in FIG. 5. As also shown in FIG. 4, the lower body portion 82 of mount 80 incorporates a pull tab 86 which protrudes therefrom to facilitate detachment of mount 80 from the interior mounting surface 42' of tanning apparatus 10.

Having described the preferred construction for representative handles 60 and 61, their use in conjunction with tanning apparatus 10 may now be better appreciated with reference to FIGS. 1 and 6. Once a user has situated himself/herself within tanning apparatus 10, handles 60 and 61 can be selectively positioned on a respective mounting surface 42' or 42" and grasped by the individual to support his/her arms in an elevated position relative to his/her torso. As shown in FIG. 6, representative first handle 60 when grasped by the individual's left hand provides a comfortable support for the individual's hand and arm during the tanning session. The suctioning effect provided by the first and second mounts 70 and 80 are sufficient such that handle 60 will not release when supporting the weight of the individual's hand and arm in a relaxed position. It can be appreciated, then, that when the individual is in a reposed tanning position within tanning apparatus 10 and his/her hand supported in a relaxed and comfortable state as shown in FIG. 6, the individual's arms are supported in an elevated position relative to the individual's torso such that the individual is in a tanning position wherein respective regions of the individual that are between the individual's arms and torso are exposed to the ultraviolet radiation. This serves to promote a more even distribution of tanning on the armpit regions of the individual's body since they are exposed to the radiation from ultraviolet lamps 40.

As such, the present invention also contemplates a method of promoting exposure to ultraviolet radiation on an individual's body during an artificial tanning session in a tanning apparatus, such as tanning apparatus 10 in FIG. 1. This methodology contemplates the steps of the individual initially entering into the tanning apparatus 10 and moving tanning units 20 and 30 from their open position in FIG. 1 to a closed position. Handles 60 and 61 may then be attached in a respective mounted state to an interior mounting surface of the tanning chamber and the control panel 50 activated to initiate ultraviolet radiation. Handles 60 and 61 may then be grasped by the individual in such a manner that the individual's arms are supported in an elevated position relative to the individual's torso thereby to assume a tanning position wherein respective regions of the individual that are between the individual's arms and torso are exposed to ultraviolet radiation. The individual then remains in the tanning apparatus 10 for selected period of time corresponding to a length of the tanning session. Of course, this methodology might also incorporate the steps of periodically detaching handles 60 and 61 from the interior mounting surface of tanning apparatus 10 during the tanning session and repositioning handles 60 and 61 thereby to adjust the individual's tanning position and promote exposure to ultraviolet radiation on other regions of the individual between the arms and torso.

Having described one embodiment of the handle(s) of the present invention in FIGS. 2-6, alternative constructions may now be appreciated with reference to FIGS. 8-11. For example, and with initial reference to FIG. 8, an alternative construction is shown for disposing a mount 180 on its associated leg 168 of handle 160. Here, as before, mount 180 is in the form of a suction cup including a frustoconical lower body portion 182 and an upper neck portion 184. Handle 160, as above, also incorporates a crosspiece 162 having an elongated grip portion 164 and a leg 168 joined thereto by a shoulder 169 of crosspiece 162. Crosspiece 162 is formed of a stiff plastic material as before. In this construction, however, associated leg 168 is formed to include a circumferential flange 172 and neck portion 184 includes a neck cavity 174 formed therein which is sized and adapted to receive flange 172 in a mated engagement to releasably dispose mount 180 on leg 168.

In FIG. 9 a construction is shown wherein the neck portion 284 of mount 280 includes an enlarged nub 274 which is insertable into an accommodating cavity 272 formed in leg 268. Here, also, the grip portion 264 is contoured so that it includes a plurality of finger recesses 263 for accommodating the individual's fingers to provide a comfortable support for the individual's hand when in the tanning position.

FIGS. 10 and 11 show alternative constructions for handles wherein the crosspiece is flexible in construction. In the handle 360 of FIG. 10, crosspiece 362 includes a chain 363 and a flexible sleeve 364 surrounding a majority of the length of chain 363 between opposed end links thereof. A nub 374 associated with the neck portion 384 of mount 380 is received through one end link 368 of chain 363. It should be readily appreciated that the other mount associated with handle 360 would be attached to crosspiece 362 in a like manner. Finally, FIG. 11 shows a flexible crosspiece 462 which includes a flexible cord 463 having opposed cord ends and a flexible sleeve 464 surrounding a majority of the length of cord 463. Here, mount 480 also has its neck portion 484 formed to include a nub 474 as in FIG. 10. Here, however, an associated end 468 of cord 463 is securely fastened around the reduced neck thickness of the neck portion 484 below nub 474 resulting in the attached state.

Figure 12:
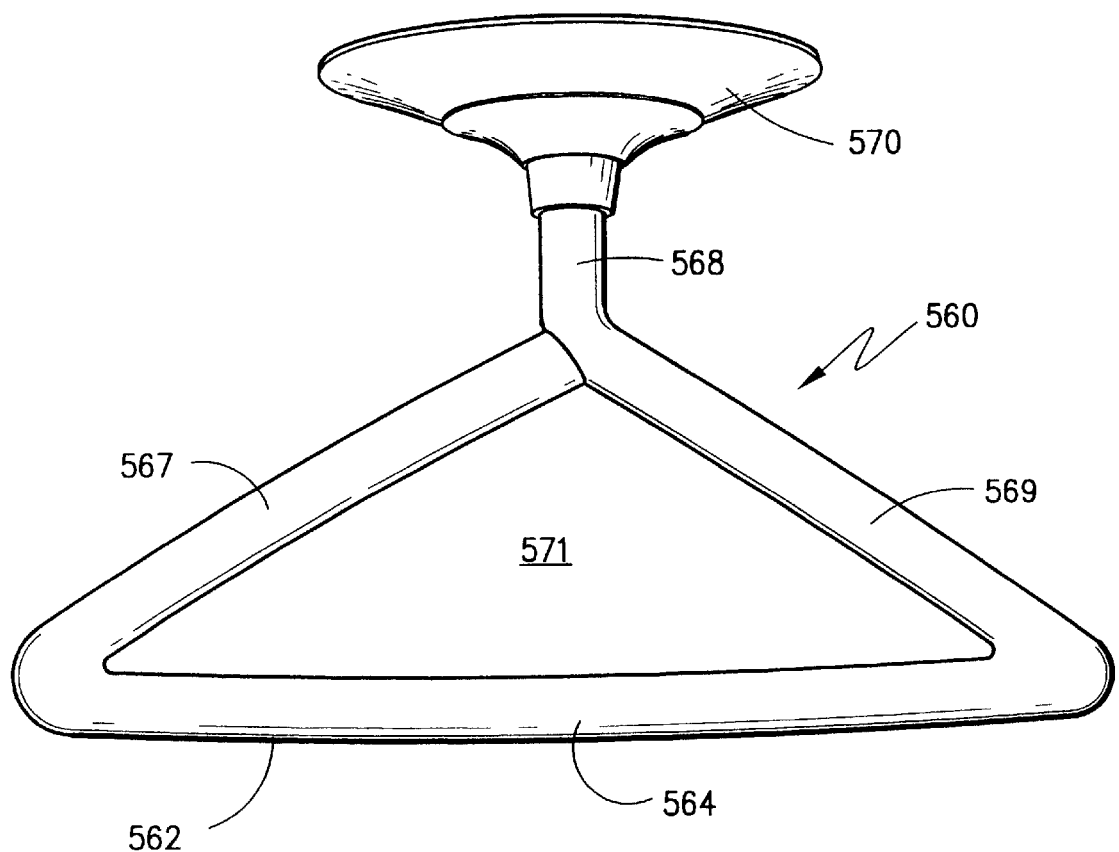
FIG. 12 is a perspective view showing a final contemplated construction for a handle according to the present invention.

Finally, FIG. 12 illustrates yet another possible embodiment for a handle 560 according to the present invention wherein handle 560 comprises a crosspiece 562 that is generally in the shape of a clothes hanger and formed from a unitary piece of plastic material or the like. Crosspiece 562 has a grasping/grip portion 564 and a pair of members 567 & 569 which converge toward one another to join at a single leg 568 on which is disposed a mount 570 in any one of the manners discussed hereinabove. As such, crosspiece 560 has an opening 571 which is sized to accommodate an individual's hand when in use.

Based on the foregoing description, it should be readily appreciated that the present invention can take on a variety of forms. In one sense, the present invention relates to one or more handles which are adapted for use by an individual during an artificial tanning session within a tanning apparatus to support the individual's arm(s) in an elevated position relative to the individual's torso. These handle(s) may take on a variety of configurations including, but limited to, the various constructions set forth in the figures. The present invention, however, also relates to a tanning apparatus, as well as an improvement to a tanning apparatus, which broadly includes first and second tanning units that are movable with respect to one another between an open position and a closed position, a plurality of ultraviolet lamps supported in one or more of the tanning units, a control panel for activating the ultraviolet lamps, and at least one handle disposed on and projecting away from a mounting surface of a selected one of the tanning units. Here, the handle broadly includes at least one mount releasably attached to the mounting surface and a grasping member connected to the mount. The grasping member is adapted to be held by the individual thereby to support one of the individual's arms in an elevated position relative to the individual's torso and promote exposure to ultraviolet radiation on a region of the individual's body between the arm and the torso during the tanning session. Further, and as also discussed above, the present invention also provides for a methodology of promoting exposure to ultraviolet radiation on a individual's body during an artificial tanning session within a tanning apparatus.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A tanning apparatus for artificially tanning an individual situated therein during a tanning session, comprising:
   a. a first elongated tanning unit adapted to be situated on a support surface, said first tanning unit having an associated first end and extending therefrom to terminate in an associated second end;
   b. an elongated second tanning unit hingedly connected to said first tanning unit and having an associated first end and extending therefrom to terminate at an associated second end, said first and second tanning units movable with respect to one another between an open position to provide access to an interior of the tanning apparatus and a closed position wherein the tanning units enclose the interior to define a tanning chamber;
   c. a plurality of first ultraviolet lamps supported between the first and second ends of a selected one of said first and second tanning units;
   d. a control switch associated with one of said first and second tanning units, said control switch operative upon activation to cause said lamps to generate ultraviolet radiation with said tanning chamber for a selected interval of time; and
   e. a first handle disposed on and projecting away from a mounting surface of a selected one of said first and second tanning units, said first handle including at least one mount releasably attached to said mounting surface and a grasping member connected to said mount, said grasping member adapted to be held by the individual thereby to support one of the individual's arms in an elevated position relative to the individual's torso and promote exposure to ultraviolet radiation on a first region of the individual's body between the arm and the torso during the tanning session.

2. A tanning apparatus according to claim 1 including a second handle disposed on and projecting away from said mounting surface, said second handle including at least one associated mount releasably connected to said mounting surface and an associated grasping member disposed on said mount, said grasping member adapted to be held by the individual thereby to support another of the individual's arms in an elevated position relative to the individual's torso and promote exposure to ultraviolet radiation on an associated second region of the individual's body between the arm and the torso during the tanning session.

3. A tanning apparatus according to claim 2 wherein each said grasping member is formed as an elongated crosspiece that extends along a respective longitudinal axis, said crosspiece including a grip portion and a pair of legs extending from respective ends of said grip portion.

4. A tanning apparatus according to claim 3 wherein each of said handles includes a plurality of mounts, a first one said mounts disposed on one of said legs and a second one of said mounts disposed on another of said legs.

5. A tanning apparatus according to claim 4 wherein each of said mounts is formed as a suction cup that includes a frustoconical lower body portion adapted to releasably suction to the interior mounting surface of the tanning apparatus and an upper neck portion adapted to engage to an associated one of said legs.

6. A tanning apparatus according to claim 5 wherein each of said legs includes an associated surrounding flange and wherein each said upper neck portion has a cavity formed therein which is sized and adapted to receive an associated said flange so that said mounts is releasably disposed on their associated legs.

7. A tanning apparatus according to claim 5 wherein each of said legs is formed to include leg cavity and wherein each neck portion includes a nub that is releasably inserted into an associated said leg cavity.

8. In a tanning apparatus which includes a pair of tanning units movable with respect to one another between an open position to provide access to an interior of the tanning apparatus and a closed position wherein said tanning units enclose said interior to define a tanning chamber, a plurality of ultraviolet lamps supported between opposed ends of at least one of said first and second tanning units, and a control switch operative upon activation to generate ultraviolet radiation with said tanning chamber for a selected interval of time, the improvement comprising a pair of handles releasably attached to an interior mounting surface of said tanning apparatus, each of said handles including a mount that is releasably attached to said mounting surface and a grasping member disposed on said mount, each said grasping member adapted to be grasped by the individual during an artificial tanning session within the tanning apparatus to support the individual's arms in an elevated position relative to the individual's torso and promote exposure to ultraviolet radiation on regions of the individual between the arms and the torso.

9. The improvement of claim 8 wherein each of said mounts is formed as a suction cup adapted to releasably suction to the interior mounting surface of the tanning apparatus.

10. The improvement of claim 9 wherein each suction cup includes a frustoconical lower body portion adapted to releasably suction to the interior mounting surface of the tanning apparatus and an upper neck portion adapted to engage an associated said grasping portion.

11. A method of promoting exposure to ultraviolet radiation on an individual's body during an artificial tanning session in a tanning apparatus, wherein said tanning apparatus includes a pair of tanning units movable with respect to one another between an open position to provide access to an interior of the tanning apparatus and a closed position wherein said tanning units enclose said interior to define a tanning chamber, a plurality of ultraviolet lamps supported by at least one of said tanning units, and a control panel operative upon activation to cause said lamps to generate ultraviolet radiation within the tanning chamber for a selected interval of time corresponding to a tanning session, said method comprising the steps of:
   a. entering said tanning apparatus;
   b. moving said tanning units from the open position to the closed position;
   c. attaching each of a pair of handles in a respective mounted state to an interior mounting surface of said tanning chamber;
   d. activating said control panel thereby to initiate said ultraviolet radiation;
   e. grasping each of said handles in such a manner that the individual's arms are supported in an elevated position relative to the individual's torso thereby to assume a tanning position wherein respective regions of the individual that are between the individual's arms and torso are exposed to the ultraviolet radiation; and
   f. remaining in the tanning apparatus for a selected period of time corresponding to a length of said tanning session.

12. The method according to claim 11 including the steps of periodically detaching said handles from the interior mounting surface during the tanning session and repositioning the handles on the interior mounting surface thereby to adjust the individual's tanning position and promote exposure to ultraviolet radiation on other regions of the individual between the individual's arms and torso.

13. A handle adapted for use by an individual during an artificial tanning session within a tanning apparatus to support the individual's arm in an elevated position relative to the individual's torso, wherein said tanning apparatus includes a pair of tanning units movable with respect to one another between an open position to provide access to an interior of the tanning apparatus and a closed position wherein the tanning units enclose the interior to define a tanning chamber, said handle comprising:
   a. an elongated crosspiece including a grip portion that extends along a longitudinal axis, and a pair of legs each extending from a respective end of said grip portion;
   b. a first mount disposed on one of said legs; and
   c. a second mount disposed on another of said legs, each of said mounts operative to releasably attach to an interior mounting surface of said tanning apparatus so that said handle can be selectively positioned on said mounting surface and grasped by the individual to support the individual's arm in an elevated position relative to the individual's torso and promote exposure to ultraviolet radiation on a region of the individual's body between the arm and the torso during the tanning session.

14. A handle according to claim 13 wherein each of said legs extends from said grip portion in a direction transverse to said longitudinal axis.

15. A handle according to claim 13 wherein said crosspiece is constructed of a rigid material.

16. A handle according to claim 13 wherein said crosspiece is flexible in construction.

17. A handle according to claim 16 wherein said crosspiece includes a flexible cord having opposed cord end portions secured to said first and second mounts, respectively.

18. A handle according to claim 17 wherein said crosspiece further includes a flexible sleeve surrounding a majority of a length of said cord between said opposed cord end portions.

19. A handle according to claim 16 wherein said crosspiece includes a chain having opposed end links attached to said first and second mounts, respectively, and a flexible sleeve surrounding a majority of a length of said chain between said opposed end links.

20. A handle according to claim 13 wherein each of said mounts is formed as a plastic suction cup.

21. A handle according to claim 20 wherein each said suction cup includes a frustoconical lower body portion adapted to releasably suction to the interior mounting surface of the tanning apparatus and an upper neck portion adapted to engage to an associated one of said legs.

22. A handle according to claim 19 wherein each of said legs includes an associated surrounding flange and wherein each said upper neck portion has a cavity formed therein which is sized and adapted to receive an associated said flange so that each of said mounts is releasably disposed on an associated one of said legs.

23. A handle according to claim 20 wherein each of said legs is formed to include leg cavity and wherein each neck portion includes a nub that is releasably inserted into an associated said leg cavity.

24. A handle according to claim 13 including a pull tab protruding from each said lower body portion, said pull tab operative upon manipulation by the individual to facilitate detachment of said mount from the interior mounting surface.

25. A handle according to claim 13 wherein each of said legs is secured to its associated said mount by a fastening element.

26. A handle according to claim 13 wherein said grip portion is contoured to include a plurality of recesses for accommodating the individual's fingers.

* * * * *